(12) United States Patent  
Aoki (10) Patent No.: US 9,863,968 B2  
(45) Date of Patent: Jan. 9, 2018

(54) CONTROL APPARATUS FOR AUTOMATIC ANALYZER

(71) Applicant: SHIMADZU CORPORATION, Kyoto-shi, Kyoto (JP)

(72) Inventor: Kengo Aoki, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 199 days.

(21) Appl. No.: 14/669,094

(22) Filed: Mar. 26, 2015

(65) Prior Publication Data

US 2015/0276773 A1 Oct. 1, 2015

(30) Foreign Application Priority Data

Mar. 27, 2014 (JP) ................. 2014-066815

(51) Int. Cl.
   - *G01N 35/00* (2006.01)
   - *B01J 19/00* (2006.01)
   - *G05B 15/02* (2006.01)
   - *G01N 35/04* (2006.01)

(52) U.S. Cl.
   CPC ... *G01N 35/0092* (2013.01); *G01N 35/00732* (2013.01); *G05B 15/02* (2013.01); *G01N 2035/0094* (2013.01); *G01N 2035/00831* (2013.01); *G01N 2035/00851* (2013.01); *G01N 2035/00891* (2013.01); *G01N 2035/0493* (2013.01)

(58) Field of Classification Search
   CPC ............................................. G01N 2035/0091  
   See application file for complete search history.

(56) References Cited

U.S. PATENT DOCUMENTS

| | | | |
|---|---|---|---|
| 7,247,277 B1* | 7/2007 | Inoue ................... | B01J 19/0046 422/130 |
| 2004/0175760 A1* | 9/2004 | Crevier ................ | B01J 19/0046 435/7.1 |
| 2008/0263468 A1* | 10/2008 | Cappione ......... | G01N 35/00722 715/771 |

FOREIGN PATENT DOCUMENTS

| | | |
|---|---|---|
| JP | 2011-185826 A | 9/2011 |
| JP | 2012-163334 A | 8/2012 |

OTHER PUBLICATIONS

"UF-Amino Station LC/MS Fast Amino Acid Analysis System" Shimadzu Corporation, Searched on Feb. 26, 2014.

* cited by examiner

*Primary Examiner* — P. Kathryn Wright  
(74) *Attorney, Agent, or Firm* — Sughrue Mion, PLLC (57) ABSTRACT

Vials (samples) as analysis targets to be set in a batch table for serial analyses are allowed to be designated simply and highly flexibly. On a batch table setting screen 100, a sample region designation method selecting button 120, an analysis direction selecting button 121, a plate image display area 125 and other components are arranged. A sample region designation method and an analysis direction are selected simply by clicking the buttons. The start position and the end position of analyses are designated by a drag-and-drop operation using a mouse on a plate image displayed in the plate image display area 125. The vials selected during a process of the drag-and-drop operation are displayed in a color discriminable from other vials. Accordingly, a simple, graphical operation can create a batch table in which the multiple vials mounted on the sample plate are set as analysis targets in a desired order.

9 Claims, 10 Drawing Sheets

- ALREADY SET UNKNOWN SAMPLE
- ALREADY SET STANDARD SAMPLE
- SELECTED UNKNOWN SAMPLE
- SELECTED STANDARD SAMPLE

[LOWER LEFT ORIGIN]

| SAMPLE REGION DESIGNATION METHOD | ONE-DIMENSIONAL TYPE DESIGNATION | | | | TWO-DIMENSIONAL TYPE DESIGNATION | | | |
|---|---|---|---|---|---|---|---|---|
| ANALYSIS DIRECTION | VERTICAL ONE-WAY DIRECTION | VERTICAL TWO-WAY DIRECTION | HORIZONTAL ONE-WAY DIRECTION | HORIZONTAL TWO-WAY DIRECTION | VERTICAL ONE-WAY DIRECTION | VERTICAL TWO-WAY DIRECTION | HORIZONTAL ONE-WAY DIRECTION | HORIZONTAL TWO-WAY DIRECTION |
| CURRENT POSITION VIEWED FROM START POSITION — RIGHT | ○ | ○ | ○ | ○ | ○ | ○ | ○ | ○ |
| UPPER RIGHT | ○ | ○ | ○ | ○ | ○ | ○ | ○ | ○ |
| UPPER | ○ | ○ | ○ | ○ | ○ | ○ | ○ | ○ |
| UPPER LEFT | × | × | ○ | ○ | × | × | × | × |
| LEFT | × | × | × | × | × | × | × | × |
| LOWER LEFT | × | × | × | × | × | × | × | × |
| LOWER | × | ○ | × | × | × | × | × | × |
| LOWER RIGHT | ○ | × | × | × | × | × | × | × |

○ : PERMITTED MOVABLE REGION
× : MOVEMENT-PROHIBITED REGION

| | VIAL NO. | TRAY | SAMPLE NAME | SAMPLE ID | SAMPLE TYPE | METHOD FILE |
|---|---|---|---|---|---|---|
| 1 | 1 | 1 | | 001 | 0:UNKNOWN | etc1¥TestMethod.lcm |
| 2 | 2 | 1 | | 002 | 0:UNKNOWN | |
| 3 | 3 | 1 | | 003 | 0:UNKNOWN | |
| 4 | 4 | 1 | | 004 | 0:UNKNOWN | |
| 5 | 5 | 1 | | 005 | 1:STANDARD | |
| 6 | 6 | 1 | | 006 | 0:UNKNOWN | |

CONTROL APPARATUS FOR AUTOMATIC ANALYZER

TECHNICAL FIELD

The present invention relates to a control apparatus for an automatic analyzer. This apparatus controls the automatic analyzer, which combines an auto-sampler for automatically selecting and taking a sample from among many previously prepared samples and an analyzer for analyzing the sample taken by the auto-sampler, and serially performs analyses.

BACKGROUND ART

In the case of serially analyzing a plurality of samples through various analyzers, such as a liquid chromatograph (LC) and a gas chromatograph (GC), an auto-sampler is typically used that sequentially selects samples one after another from among many samples having been previously prepared and introduces the samples into an analyzer. In the case with liquid samples, the auto-sampler includes a sample plate on which many vials (sample containers) containing sample solution are mounted, a moving mechanism for moving the sample plate two-dimensionally or three-dimensionally, and a sample collector that includes a needle for collecting the sample solution from a vial at a predetermined position and other units (see Patent Literature 1 etc.).

Figure 13:
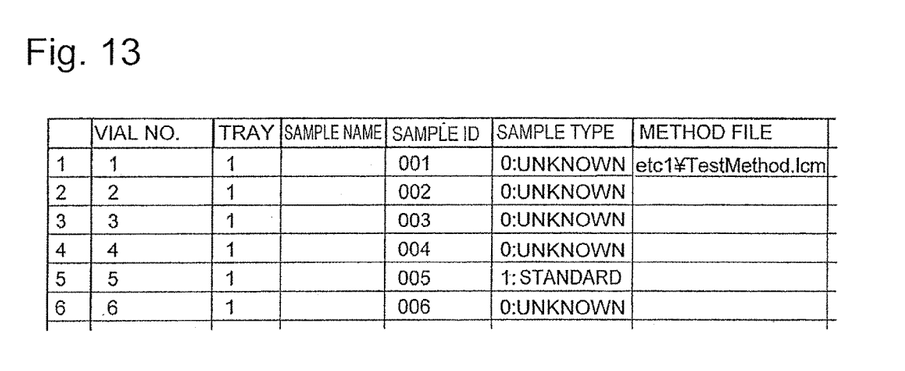
FIG. 13 is a diagram showing an example of the batch table.

In the case of automatic analyses through use of such an auto-sampler, an analysis operator mounts vials containing necessary sample solutions on the sample plate before analysis, and loads the plate into the auto-sampler. The analysis operator then designates the analysis order of the vials and analysis conditions for analyzing the samples in respective vials through a control apparatus (typically, a personal computer in which specialized control software is installed) for controlling operations of an automatic analyzer including the auto-sampler, and subsequently instructs start of analyses. More specifically, as described for example in Patent Literature 2, a batch table (analysis schedule table), in which necessary information is described, is created with respect to items such as the sample plate number (tray number in this literature), vial number, sample type, name of method file in which an analysis condition is described, and then start of serial analyses according to the batch table is instructed. FIG. 13 shows an example batch table.

Figure 14A:
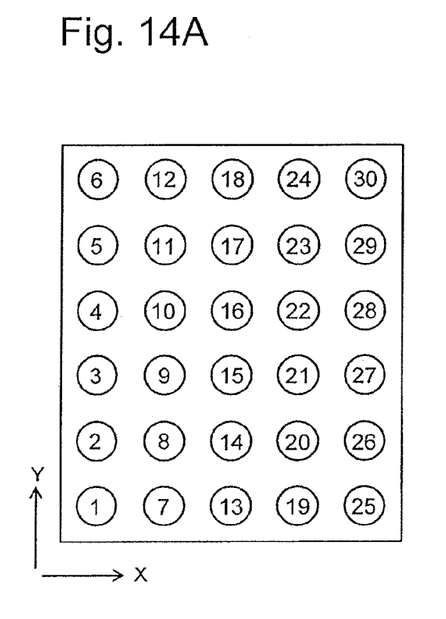
FIG. 14A and FIG. 14B are diagrams showing examples of sample plates.
Figure 14B:
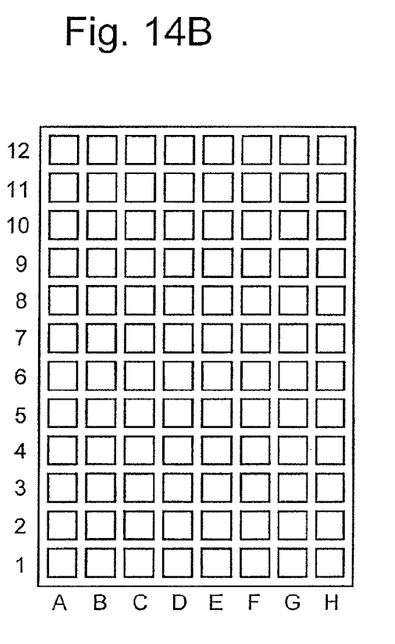

The vial number on the batch table is the number that indicates the position on the sample plate where a vial (i.e., a sample) is mounted. Numbers are previously assigned to the vial-mounting positions on the sample plate, and normally each of the numbers serves as respective vial number. FIG. 14A and FIG. 14B show examples of sample plates. FIG. 14A shows an example of a sample plate for cylindrical vials. The vial numbers are serial numbers starting from one. FIG. 14B shows an example of a sample plate for rectangular-shaped vials. The vial numbers are composed of X-directional location and Y-directional location (e.g., "A1", "F10", etc.). Some types of sample plates are prepared having different number of mountable vials.

In making a batch table, the analysis operator must designate a vial number for each row of the table corresponding to one analysis. Conventionally, the analysis operator designates the vial numbers according to one of the following three methods.

(1) The analysis operator directly inputs respective numbers as text into vial number fields of the batch table as shown in FIG. 13. Hereinafter, this method is referred to as "direct input method".

(2) When the analysis operator inputs necessary data including the analysis start position on the sample plate and the number of samples into preset fields on an input auxiliary screen, such a wizardry window, the input data is processed to fill vial numbers in a batch table (see Non Patent Literature 1). Hereinafter, this method is referred to as "auxiliary screen-using method".

(3) The analysis operator inputs data using a graphical user interface, such as a plan view of a sample plate, with a pointing device like a mouse on the display screen. Hereinafter, this method is referred to as "GUI-using method".

The GUI-using method has an advantage compared to the other two methods in allowing the analysis operator to intuitively operate the apparatus, so that, in recent years, the GUI-using method has become widely used. According to the GUI-using method, if the operation is made in a quite standard way, for example, using the sample plate shown in FIG. 14A, setting the vial numbers are designated serially in an ascending order without skip, the operation by the analysis operator is simple and user-friendly. However, if analyses in a special order or in special situations are needed, significantly complicated operations are required. Examples of such cases are listed below.

<The Case where Analyses Order on Sample Plate is not Standard>

As described above, when analyses are performed designating vial numbers in the ascending order without skip, the direction of selecting the vials, that is, the analysis direction, is the vertical direction in the case of the sample plate shown in FIG. 14A. Specifically, the direction is the vertical one-way direction from the bottom to the top (Y direction in FIG. 14A). Accordingly, in the case of serially analyzing, for example, 15 samples using the sample plate of FIG. 14A, target samples (vials) are mounted at positions having vial number [1] to vial number [15] (hereinafter, the vial number on the sample plate is indicated by [*]). However, if a multi-channel pipette, which is composed of horizontally arranged multiple pipettes, is used, samples are taken in the order of vial numbers [1], [7], [13], . . . , that is, in the horizontal direction (X direction in FIG. 14A and FIG. 14B), and analyses should be performed in the same order. In such a case of analyses in which the order is out of standard, setting according to the conventional GUI-using method becomes complicated.

<The Case where Samples Set within a Two-Dimensional Region on Sample Plate is to be Analyzed>

To avoid temperature change of samples set on the sample plate, the temperature of the sample plate loaded in the auto-sampler is normally controlled by a heater unit or the like. However, the temperature of the sample plate is not adequately controlled flat over the entire area: the peripheral region of the sample plate tends to have lower temperature than the central region. Accordingly, in some cases, placing samples at vial-mounting positions, for example, on the outer-most areas of the sample plate is avoided. In such cases, it is necessary to selectively analyze samples in a desired two-dimensional region on the sample plate. However, also in these cases, setting is complicated according to the conventional GUI-using method.

<The Case where Auto-Sampler Capable of Installing Multiple Sample Plates is Used>

In some type of auto-samplers, a plurality of sample plates can be installed, and a series of analyses can be performed across the sample plates. In such cases, the vial numbers on the batch table are required to be designated together with the number of the sample plate such as, for example, vial number [1] on the second sample plate, vial number [16] on the fourth sample plate, etc.

In many cases according to the aforementioned direct input method, auxiliary screen-using method, and some types of GUI-using methods, besides the screen and fields for setting the vial number, another screen and fields for setting the sample plate number is provided, and the sample plate number can be designated through the screen and fields. It is, however, difficult for the analysis operator to intuitively grasp which vial-mounting position of which sample plate is designated. This causes a problem in that the operator tends to have trouble in setting, or sometimes make wrong settings.

CITATION LIST

Patent Literature

Patent Literature 1: JP 2012-163334 A
Patent Literature 2: JP 2011-185826 A

Non Patent Literature

Non Patent Literature 1: "UF-Amino Station LC/MS Fast Amino Acid Analysis System" Shimadzu Corporation [searched on Feb. 26, 2014], Internet.

SUMMARY OF INVENTION

Technical Problem

The present invention is made in view of the above problems, and has a main object to provide a control apparatus for an automatic analyzer which achieves high flexibility in setting the order of samples (vials) for serial analyses, while responding to various requests from analysis operators and improves operability by simplifying operations and procedures for the settings.

Solution to Problem

The present invention made to solve the above problems is a control apparatus for an automatic analyzer including an auto-sampler and an analyzer, where the auto-sampler sequentially selects samples one after another previously prepared on a sample plate on which samples are mountable two-dimensionally in rows and columns and take at least a part of the samples, and the analyzer analyzes the taken samples, the control apparatus including:

a) a display processor configured to display a plate image indicating a shape of the sample plate used for analysis and sample-mountable positions on the sample plate, on a screen of a display unit;

b) a first selector configured to allow an analysis operator to select at least one of a one-dimensional designation type and a two-dimensional designation type as a designation method by the analysis operator to designate an analysis target region where the samples to be subjected to serial analyses are mounted on the sample plate;

c) a second selector configured to allow the analysis operator to select an analysis direction on the sample plate during the serial analyses from among a plurality of options;

d) a start/end position recognizer configured to recognize a start position of a sample on the sample plate where the serial analyses are started according to a first operation performed by the analysis operator using a pointing device on the plate image displayed on the screen of the display unit, and to recognize an end position of a sample on the sample plate where the serial analyses are finished according to a second operation performed by the analysis operator using the pointing device on the plate image;

e) a sample-number calculator configured to calculate the number of samples to be serially analyzed based on the analysis target region designation method selected by the first selector, the analysis direction selected by the second selector, and the start position and the end position recognized by the start/end position recognizer; and f) a batch table creator configured to create a batch table including descriptions about control information for performing the serial analyses and to identify respective identification numbers of mounting positions on the sample plate of the samples to be analyzed in the serial analyses, based on the analysis target region designation method selected by the first selector, the analysis direction selected by the second selector, the start position and the end position recognized by the start/end position recognizer, and the number of samples calculated by the sample-number calculator, and sets the identification numbers on respective rows of the batch table.

The control apparatus for the automatic analyzer according to the present invention typically has a configuration that predetermined control software is installed in a personal computer provided with an operation unit, a display unit, etc.

In the case where, for example, the analyzer is a liquid chromatograph and the analysis target is sample solution, the "sample" is a "vial" containing sample solution.

In the control apparatus for the automatic analyzer according to the present invention, when the analysis operator newly create a batch table or adds new analyses to an existing batch table, the analysis operator selects either a one-dimensional designation type or a two-dimensional designation type as a method of designating the analysis target region through the first selector. The "one-dimensional designation type" is an option for designating a linear region from the start position to the end position (continuing to the next row or column upon reaching an end of the region) as the analysis target region on the sample plate. The "two-dimensional designation type" is an option for designating, as an analysis target region on the sample plate, a rectangular region with diagonal vertices at the start position and the end position.

The analysis operator selects the analysis direction on the sample plate through the second selector. Options of analysis directions include at least the row direction and the column direction. For example, in the case of the row direction, further options may be provided, such as one-way same direction (repetition) and turn-around two-way directions.

The first and second selectors may use a "button" or a "radio button", which are typical graphical user interface (GUI) components.

Furthermore, the analysis operator performs a first operation and a second operation using a pointing device, such as a mouse, on the plate image displayed on the screen of the display unit. For example, the first operation may be an operation of pressing down a mouse button, and the second operation may be an operation of releasing the pressed mouse button. The start/end position recognizer recognizes the start position and the end position of the serial analyses according to positions where such operations through use of the pointing device are performed. When the method of designating the analysis target region and the analysis direction are determined and the start position and the end position are further determined, the positions of all the samples to be sequentially selected on the sample plate during the serial analyses are determined. The sample-number calculator then calculates the number of samples to be serially analyzed.

The batch table creator identifies the identification numbers (e.g., vial numbers) indicating the mounting positions of samples to be analyzed in respective analyses of the serial analyses from the information, and sets the numbers in the respective rows of a newly created batch table or in the respective rows newly added to an existing batch table.

As described above, according to the control apparatus for the automatic analyzer according to the present invention, simple operations through use of a pointing device, such as a mouse, can create the batch table according to which the samples on the sample plate are sequentially selected in any of various orders and subjected to analyses.

A preferable specific form of the control apparatus for the automatic analyzer according to the present invention may be configured such that the display processor repeatedly calculates the region of selected samples based on a latest pointing position by the pointing device while the pointing device is being moved after the first operation for designating the start position and the end position is performed using the pointing device on the plate image, and displays the plate image such that samples determined to be selected by the calculation is visually discriminable from other samples.

More specifically, for example, it is preferred that on the plate image, the selected samples be displayed with a different color or with a different display symbol from that of the other samples. According to this configuration, when the analysis operator designates the start position and the end position, the operator can intuitively grasp the region of selected samples on the plate image, whereby erroneous selection can be prevented.

Another preferable specific form of the control apparatus for the automatic analyzer according to the present invention may be configured such that the display processor displays samples on the plate image differently (or visually discriminably) between samples already set in the existing batch table, samples not yet set in the batch table, and samples being selected for designating the start position and the end position.

Also for the discrimination, different color or different display symbol as described above may be used. This configuration can prevent erroneous operations in adding an analysis to the batch table such as double designation of samples that have already been set for another analysis in the existing batch table.

Another preferable specific form of the control apparatus for the automatic analyzer according to the present invention may be configured such that the apparatus further includes a third selector for allowing the analysis operator to select one from options of sample information on the samples, where the options include at least a standard sample and an unknown sample, and the display processor displays the plate image such that at least the standard sample and the unknown sample are visually discriminated from each other based on the sample information already set using the third selector or the sample information to be set using the third selector. The standard sample is, for example, a sample that has a known component concentration and is used to create a calibration curve.

Also for the discrimination, different color or different display symbol as described above may be used. This configuration allows the analysis operator to intuitively grasp the mounting positions of the standard sample and the unknown sample on the sample plate.

Still another preferable specific form of the control apparatus for the automatic analyzer according to the present invention may be configured such that the start/end position recognizer invalidates the second operation by the analysis operator using the pointing device when the pointing position by the pointing device is at a position out of a region that can be allowed according to the analysis direction selected by the second selector while the pointing device is being moved after the first operation is performed using the pointing device on the plate image.

If the start position is determined and the analysis direction is determined on the plate image, the region where an end position can be placed is determined. Accordingly, the start/end position recognizer determines whether the pointing position of the pointing device is out of the region where the end position can be placed or not when the analysis operator moves the pointing device. If the position is out of the region, this recognizer invalidates the second operation. Therefore, inappropriate operations that cannot appropriately set the region of samples to be analyzed can be prevented from being accepted.

It is preferable in the control apparatus for the automatic analyzer according to the present invention, the order of an operation for the selection of the analysis direction by the second selector and an operation for the designation of the start position and the end position by the start/end position recognizer can be exchanged. Therefore, when the analysis operator wrongly selects the analysis direction, the operator can correct it easily.

It is preferable in the control apparatus for the automatic analyzer according to the present invention that, besides designating a region where multiple samples are serially arranged or congregate on one sample plate, discontinuous (or separate) sample-mounted positions can be set by performing a predetermined operation.

Owing to this configuration, analyses in a more complicated order for multiple samples mounted on the sample plate can also be set through simple operations.

Preferably, the control apparatus for the automatic analyzer according to the present invention is configured such that the auto-sampler can be loaded with a plurality of sample plates, the apparatus further includes:

a fourth selector for allowing the analysis operator to select a type of the sample plate to be used for serial analyses; and a fifth selector for allowing the analysis operator to select one sample plate with reference to sample plate numbers assigned to the respective sample plates when the sample plates are loaded in the auto-sampler, and the display processor displays, on the screen of the display unit, the plate image according to the type selected by the fourth selector, when the one sample plate classified into the type is selected by the fifth selector.

According to this configuration, for example, even if multiple sample plates having different numbers of samples capable of being mounted are loaded in the auto-sampler, the analysis operator can perform an operation of determining samples to be set in the batch table while watching the plate image having the same shape and the same sample-mounted positions as those of a desired sample plate. Accordingly, any erroneous operation by the analysis operator can be prevented.

If the order of the type selecting operation by the fourth selector and the sample plate selecting operation by the fifth selector is not specified and selection can be changed at any timing, the operability is further improved.

In the case where multiple sample plates can be loaded in the auto-sampler, it is preferred to adopt a configuration where the display processor displays, on the screen of the display unit, correspondence relationship between positions of the sample plates in the auto-sampler and the respective sample plate numbers.

According to this configuration, even if the analysis operator cannot recognize the correspondence between the position of a sample plate that the analysis operator intends to use and the sample plate number, the operator can perform the operation for setting while watching the display screen and easily selecting the target sample plate. Therefore, the analysis operator is not required to check the correspondence each time between the position of the sample plate intended to be used and the sample plate number, and erroneous operations pertaining to selection of the sample plate can be reduced.

To omit operations by the analysis operator through the fourth selector and the fifth selector, it is further preferred to adopt a configuration of automatically collecting information indicating the types of the sample plates loaded in the auto-sampler and the loading position (sample plate number) from the auto-sampler. Accordingly, the control apparatus for the automatic analyzer according to the present invention is preferably configured such that the apparatus further includes an information acquisition unit that receives information on types and loading positions of one or more sample plates from the auto-sampler when the one or more sample plates are loaded in the auto-sampler, and the display processor displays the plate image corresponding to the designated sample plate number based on the information received by the information acquisition unit. This configuration negates the need for the analysis operator to manually input each time the types and loading positions of the one or more sample plates loaded in the auto-sampler, and can prevent human errors of setting.

Advantageous Effects of Invention

According to the control apparatus for the automatic analyzer according to the present invention, through simple and intuitively user-friendly graphical operations, the analysis operator can create the batch table according to which analyses are performed and change the batch table while sequentially selecting the samples on the sample plate in any of various orders. Accordingly, the workload accompanying creation and change of the batch table can be reduced, working errors tend not to occur, and the working efficiency is improved.

DESCRIPTION OF EMBODIMENTS

Figure 1:
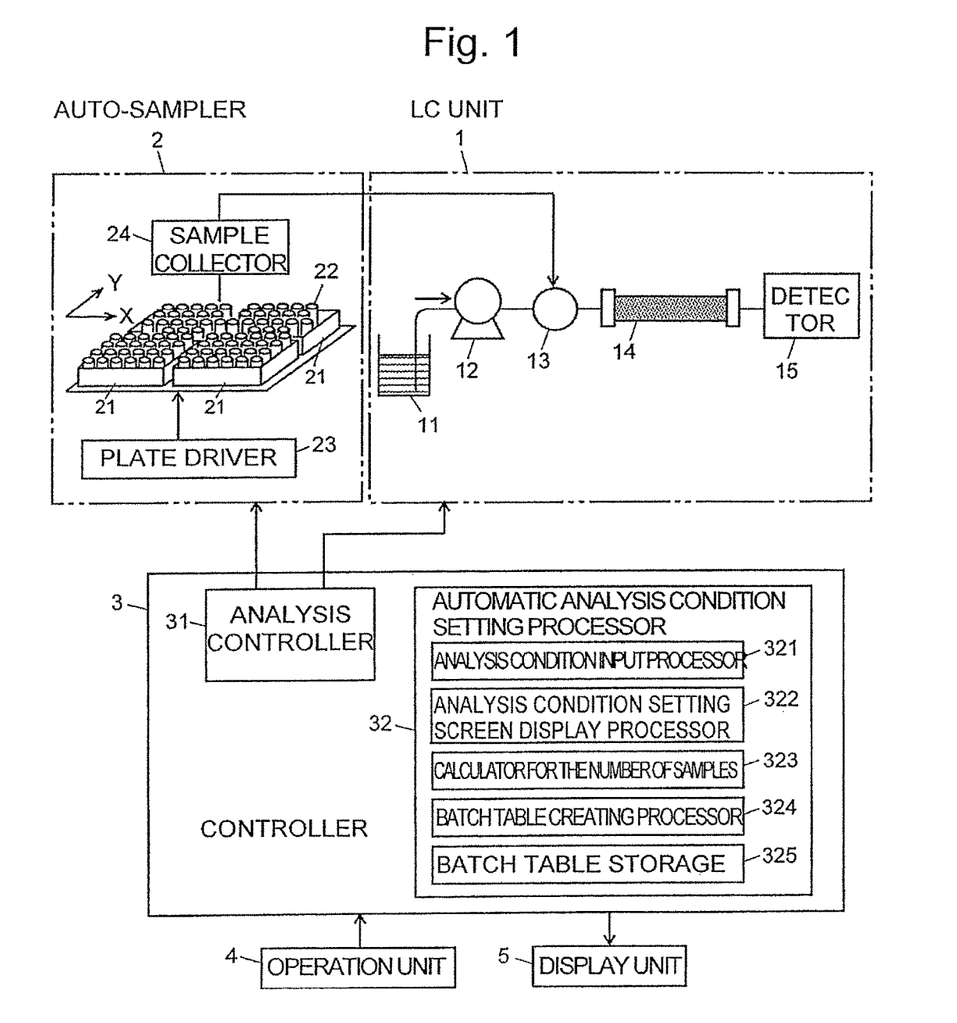
FIG. 1 is a schematic configuration diagram of an example of an LC analyzing system including a control apparatus for an automatic analyzer according to the present invention.

Hereinafter, an example of an LC analyzing system including a control apparatus for an automatic analyzer according to the present invention is described with reference to the attached drawings. FIG. 1 is a schematic configuration diagram of the LC analyzing system according to this example.

This LC analyzing system includes a liquid chromatograph (LC) unit 1 that temporally separates and detects contained components (compounds) in sample solution, an auto-sampler 2 that selects many previously prepared vials one after another, takes a predetermined amount of sample solution in the vials, and supplies the solution to the liquid chromatograph unit 1, and a controller 3 that controls operations of each of these components.

The liquid chromatograph unit 1 includes a mobile phase container 11 that stores a mobile phase, a liquid supply pump 12 that suctions the mobile phase in the mobile phase container 11 and supplies the mobile phase at a substantially constant flow rate, an injector 13 that injects sample solution to be analyzed into the mobile phase, a column 14 that separates various components contained in the sample solution injected in the mobile phase in the time direction, and a detector 15 that sequentially detects the various components separated by the column 14. The detector 15 may be a mass spectrometer, a photodiode array (PDA) detector, an ultraviolet-visible spectrophotometric detector and the like.

The auto-sampler 2 includes a tray-shaped sample plate 21 on which many vials 22 each containing sample solution (only solvent containing no sample component in some cases) are mounted, a plate driver 23 that moves the sample plate 21 in an X axis direction and a Y axis direction which are orthogonal to each other, and a sample collector 24 that includes a syringe and a syringe elevating and lowering mechanism and suctions a predetermined amount of sample solution in the vial 22 at a predetermined sample suction position. The sample solution taken by the sample collector 24 is supplied to the injector 13 of the liquid chromatograph unit 1, and injected into the mobile phase or discharged to an effluent unit, not shown (in the case of aiming at cleaning a flow path and the like).

In the case of the auto-sampler 2 in this example, a plurality of (four in FIG. 1) sample plates can be installed on a plane, the syringe of the sample collector 24 is movable between the sample plates. In some cases, an auto-sampler may have a configuration including a changer for automatically replacing sample plates. Alternatively, an auto-sampler that can be provided with only one sample plate may be used.

The controller 3, to which an operation unit 4 and a display unit 5 are connected as user interfaces, includes an analysis controller 31 that transmits control signals to the liquid chromatograph unit 1 and the auto-sampler 2 for performing analyses, and an automatic analysis condition setting processor 32 as functional blocks.

The automatic analysis condition setting processor 32 includes an analysis condition input processor 321, an analysis condition setting screen display processor 322, a calculator 323 for the number of samples, a batch table creating processor 324, and a batch table storage 325, as functional blocks. The controller 3 may have a configuration that includes a personal computer as hardware resources, and can achieve the functions of the respective blocks through execution on the computer of specialized control software previously installed on the computer.

As shown in FIG. 1, the LC analyzing system of this example can automatically and sequentially analyze the sample solution in many vials 22 prepared on the sample plate 21 loaded in the auto-sampler 2. To perform such serial analyses, an analysis operator is required to previously create a batch table in which control information including the analysis order and analysis conditions are described. The analysis operator (operator) is required to previously mount vials containing sample solution necessary for a series of serial analyses on appropriate positions on the sample plate 21. The automatic analysis condition setting processor 32 performs characteristic processes and control, which will be described below, in order to allow such preparatory operations for serial analyses to be efficiently and simply performed.

Figure 2:
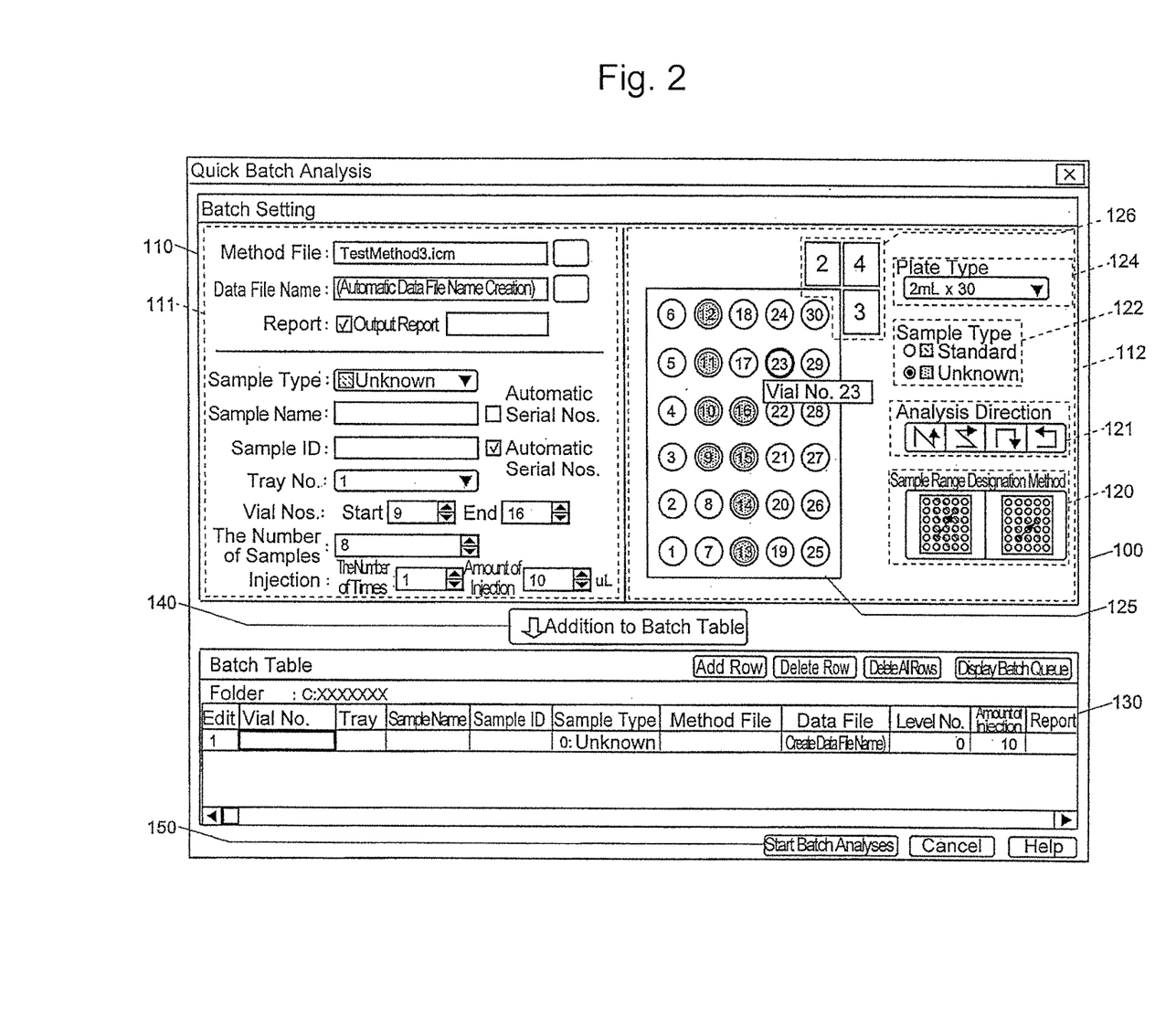
FIG. 2 is a diagram showing an example of an operation screen for creating a batch table in the LC analyzing system of this example.
Figure 3:
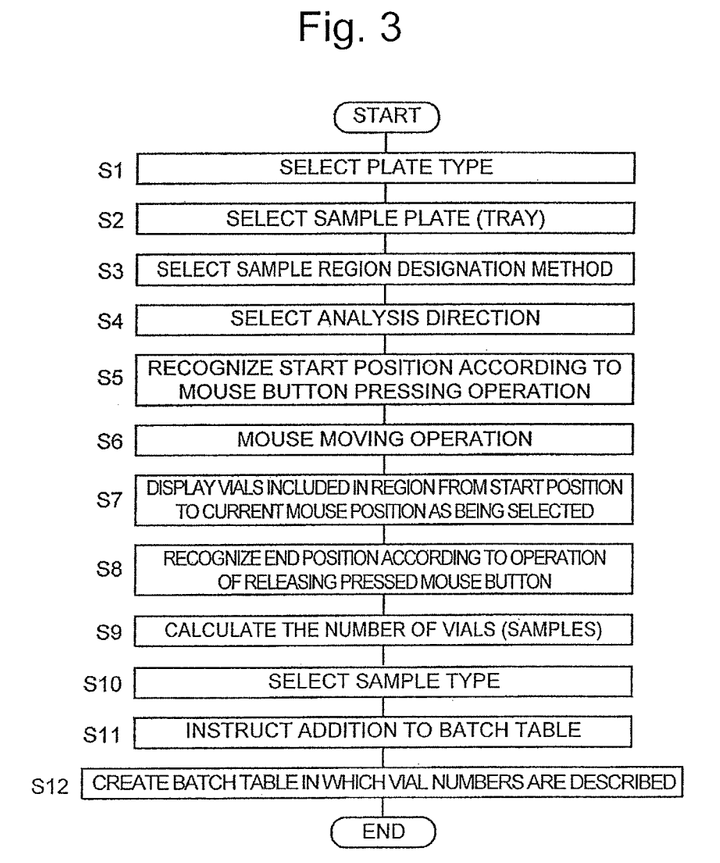
FIG. 3 is a flowchart showing an example of operation procedures and processing procedures for creating the batch table in the LC analyzing system of this example.

FIG. 2 is a diagram showing an example of an operation screen for creating the batch table in the LC analyzing system of this example. FIG. 3 is a flowchart showing an example of operation procedures and processing procedures for creating the batch table.

When the analysis operator performs predetermined operations for setting the batch table through the operation unit 4, the analysis condition setting screen display processor 322 displays a batch table setting screen 100 as shown in FIG. 2 on the screen of the display unit 5.

First, the screen configuration of the batch table setting screen 100 is described. As shown in FIG. 2, a batch setting area 110 is provided in an upper area of the batch table setting screen 100, and a batch table display area 130 is provided in a lower area of the batch table setting screen 100. A batch table creation instructing button 140 is provided between the batch setting area 110 and the batch table display area 130. This button is for making an instruction for adding contents set in the batch setting area 110 to the batch table, or for creating a batch table having contents set in the batch setting area 110 if no batch table has been created yet. Below the batch table display area 130, a batch analysis start instructing button 150 for making an instruction for execution of analyses according to the set batch table is provided.

In a left area of the batch setting area 110, a text information input area 111 in which various types of information to be set in the batch table are input in a text format or set through selection of a pull-down list is provided. In a right area of the batch setting area 110, a graphical information input area 112 for inputting most of pieces of information that can be input in the text information input area 111 through graphical operations is provided.

The graphical information input area 112 contains sample region designation method selecting buttons 120, analysis direction selecting buttons 121, sample type selecting buttons 122, a plate type selecting box 124, a plate image display area 125, sample plate number selecting buttons 126 and other components.

The sample region designation method selecting button 120 is a button for selecting either one of a "one-dimensional designation type" and a "two-dimensional designation type" each shown in icon. The analysis direction selecting button 121 is a button for selecting either one of a "vertical one-way direction", a "horizontal one-way direction", a "vertical two-way direction" and a "horizontal two-way direction" each shown in icon. The sample type selecting button 122 is a radio button for selecting either one of an unknown sample and a standard sample. The plate type selecting box 124 is a pull-down list for selecting a sample plate type. The plate image display area 125 is a region for displaying a plate image corresponding to the sample plate selected through the sample plate number selecting button 126. The sample plate number selecting button 126 is a button for selecting one sample plate to be displayed on the plate image display area 125 among sample plates loaded in the auto-sampler 2.

After the aforementioned batch table setting screen 100 is displayed, the analysis operator selects a type of a sample plate (plate type) to be used in the plate type selecting box 124 (step S1), and then selects the sample plate number for use of the type of the sample plate through the sample plate number selecting button 126 (step S2). The analysis condition input processor 321 accepts such operations, and associates the sample plate number with the plate type. For the types of sample plates selectable through the plate type selecting box 124, respective plate images that indicate the shapes of the sample plates and vial-mounting positions are registered. Accordingly, as described above, after the sample plate number is associated with the plate type, the plate image corresponding to the sample plate selected through the sample plate number selecting button 126 is drawn in the plate image display area 125. In this case, the type of the sample plate shown in FIG. 14A is used. Alternatively, if the type of the sample plate shown in FIG. 14B is selected, a plate image analogous to that of FIG. 14B is drawn in the plate image display area 125.

The example of FIG. 2 shows a state where the sample plate having the sample plate number "1" is selected from among four sample plates loaded in the auto-sampler 2, and the plate image of the plate type associated with the sample plate is drawn in the plate image display area 125. Operations and processing in and after step S3 are performed on the sample plate selected here. In other words, if the sample plate is changed through the sample plate number selecting button 126, the sample plate to be operated or processed in and after step S3 is changed.

Upon a click operation on any of the sample region designation method selecting buttons 120 by the analysis operator, the analysis condition input processor 321 accepts this operation, and selects any of the "one-dimensional designation type" and "two-dimensional designation type" as the sample region designation method (step S3). The "one-dimensional designation type" is an option that causes the analysis target region on the sample plate to be a linear region from the start position to the end position. The "two-dimensional designation type" is an option that causes the analysis target region on the sample plate to be a rectangular region having diagonal vertices at the start position and the end position.

Next, upon a click operation on any of the analysis direction selecting buttons 121 by the analysis operator, the analysis condition input processor 321 accepts this operation, and selects any of the "vertical one-way direction", "horizontal one-way direction", "vertical two-way direction" and "horizontal two-way direction" as the analysis direction (step S4).

Figure 6:
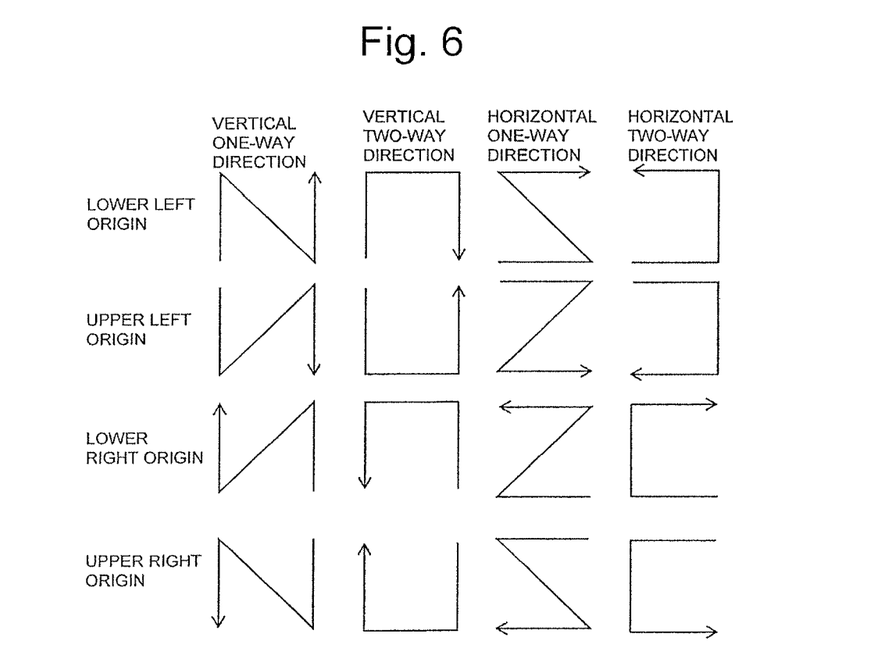
FIG. 6 is a diagram showing all types of analysis directions that can be designated on the sample plate.

Here, the analysis direction is described with reference to FIG. 6. FIG. 6 is a diagram showing all conceivable types of analysis directions on the sample plate. As a start point for defining the analysis direction, four types including a lower left origin, an upper left origin, a lower right origin and an upper right origin can be conceived. For each of the types, four types including a vertical one-way direction, a vertical two-way direction, a horizontal one-way direction and a horizontal two-way direction can be conceived.

The vertical one-way direction and the horizontal one-way direction indicate a method that sequentially designates vials one after another in a predetermined region set on the sample plate, and does not turn back upon reaching an end of the region, but moves to the head of the next row or to the head of the next column, and continues to designate vials in the same direction, that is, in a one-directional manner. On the other hand, the vertical two-way direction and the horizontal two-way direction indicate a method that sequentially designates vials one after another in a predetermined region set on the sample plate, and upon reaching an end of the region, moves to the next row or the next column in the region and turns back, that is, continues to sequentially designate vials in the direction opposite to the above case.

The conceivable analysis directions are 16 types shown in FIG. 6. However, too many options put a large load on the analysis operator. Thus, in order to narrow down the number of options for analysis direction, the LC analyzing system of this example limits the starting point for defining the analysis direction only to the "lower left origin". Accordingly, actually selectable analysis directions are only four types including the vertical one-way direction, vertical two-way direction, horizontal one-way direction and horizontal two-way direction each with the lower left origin. It is a matter of course that all of the upper left origin, the lower right origin and the upper right origin may be configured to be selectable to allow all the aforementioned 16 analysis directions to be selected. In such a case with many options, selection through a pull-down list is more useful than that through a button.

Subsequently, the analysis operator performs operations through a mouse (or another pointing device) on the plate image displayed in the plate image display area 125 to set the start position and end position for analyses. More specifically, the analysis operator disposes the pointing position of the mouse on a vial that is intended to be the start position on the plate image displayed in the plate image display area 125, and performs an operation of pressing down a mouse button. Upon receipt of this operation, the analysis condition input processor 321 recognizes, as the start position, the vial number where the pressing down operation is performed (step S5). Here, the start position and the end position have already been set. However, if there is any "selected vial" that is not set in the batch table, the setting is canceled. Next, the analysis operator performs an operation of moving the mouse on the plate image until the pointing position of the mouse reaches the vial intended to be the end position while keeping the button pressed down (step S6).

During execution of the above step S6, the analysis condition input processor 321 recognizes the pointing position of the mouse in real time, and determines whether or not the pointing position is in a permitted movable region defined according to the sample region designation method selected in step S3 and the analysis direction selected in step S4. If the position is not in the permitted movable region, the mouse operation is determined to be invalid.

Figure 5:
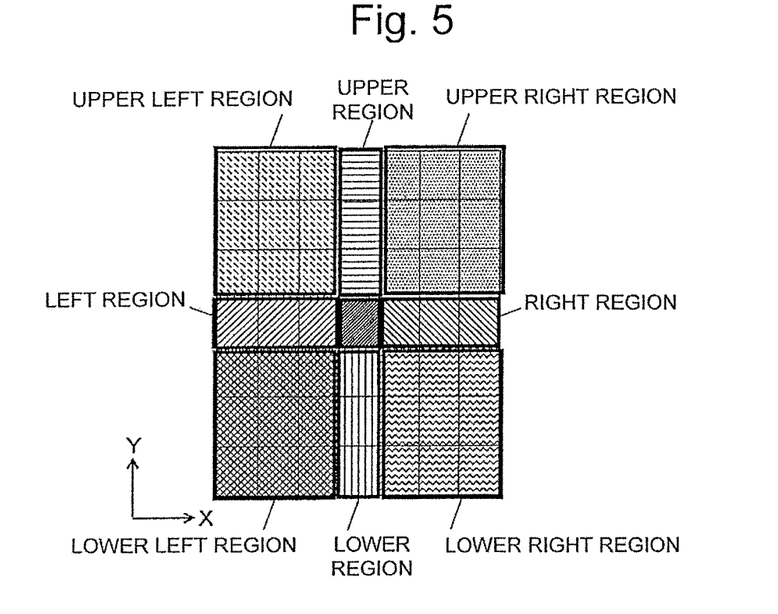
FIG. 5 is a diagram showing a specific position and the names of peripheral regions on the sample plate in the LC analyzing system of this example.
Figure 7:
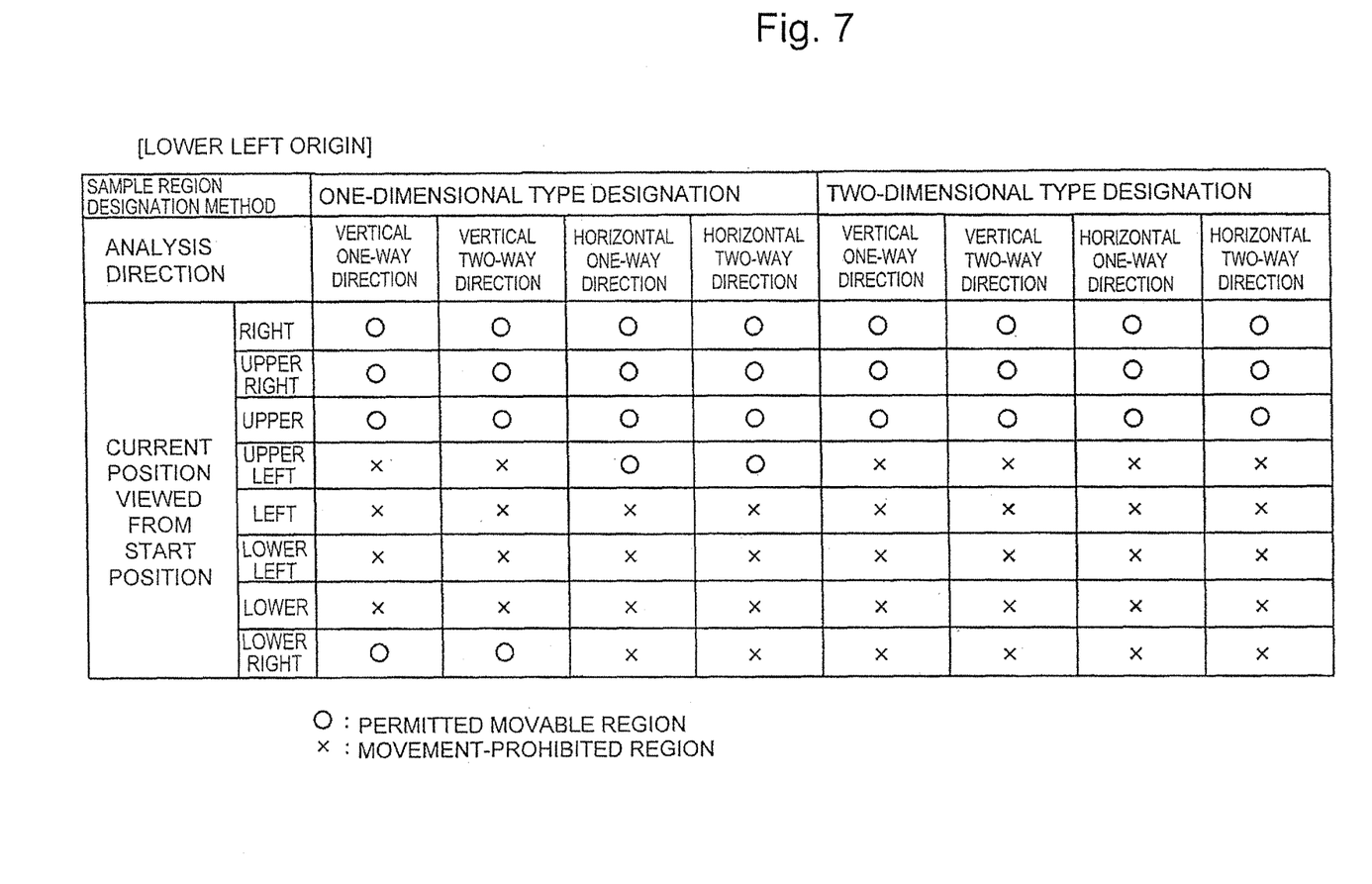
FIG. 7 is a diagram showing whether the end position can be set or not with respect to the start position in the case of the lower left origin.

FIG. 5 is a diagram showing a specific position and the names of its peripheral regions on the sample plate. FIG. 7 is a diagram showing the setting availabilities of end positions for the start positions in the case of the lower left origin. If the center position is the start position in FIG. 5, it can be considered that eight regions reside around the position; the regions are a right region, an upper right region, an upper region, an upper left region, a left region, a lower left region, a lower region, and a lower right region.

For example, if the "one-dimensional designation type" is selected as the sample region designation method and the "vertical one-way direction" is selected as the analysis direction, it can be understood that only four regions that are the right region, the upper right region, the lower right region and the upper region are the permitted movable regions, and other four regions are movement-prohibited regions. Accordingly, if the pointing position of the mouse is in any of the right region, the upper right region, the lower right region and the upper region with respect to the start position in the plate image, this mouse operation is validated. If the position is in other regions, the mouse operation is invalidated. This is also applicable to the other sample region designation methods and the other analysis directions.

Figure 8:
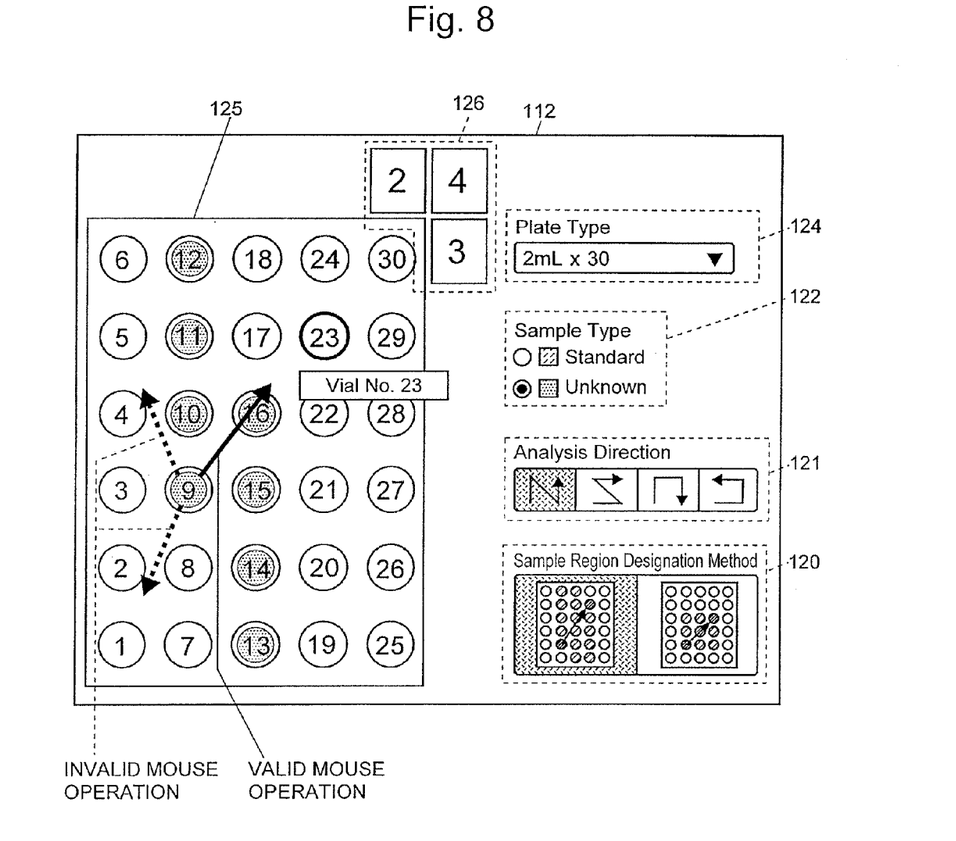
FIG. 8 is a diagram showing an example of valid and invalid mouse movements from the start position in the case of the sample region designation method: an one-dimensional designation type; and the analysis direction: a vertical one-way direction.
Figure 9:
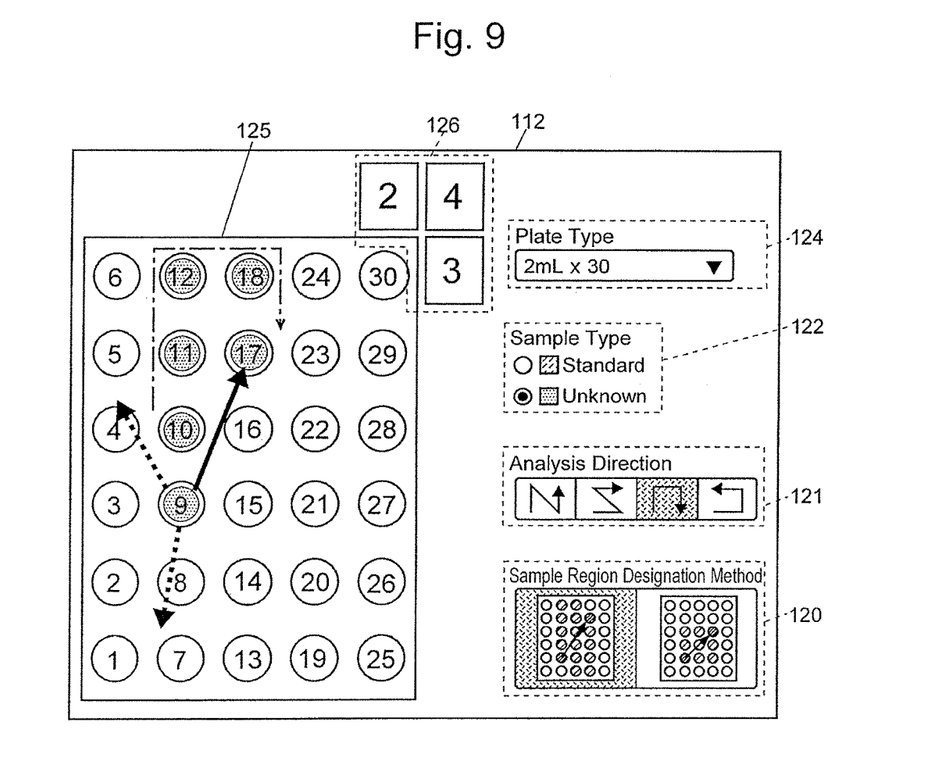
FIG. 9 is a diagram showing an example of mouse movements from the start position in the case of the sample region designation method: the one-dimensional designation type; and the analysis direction: a vertical two-way direction.
Figure 10:
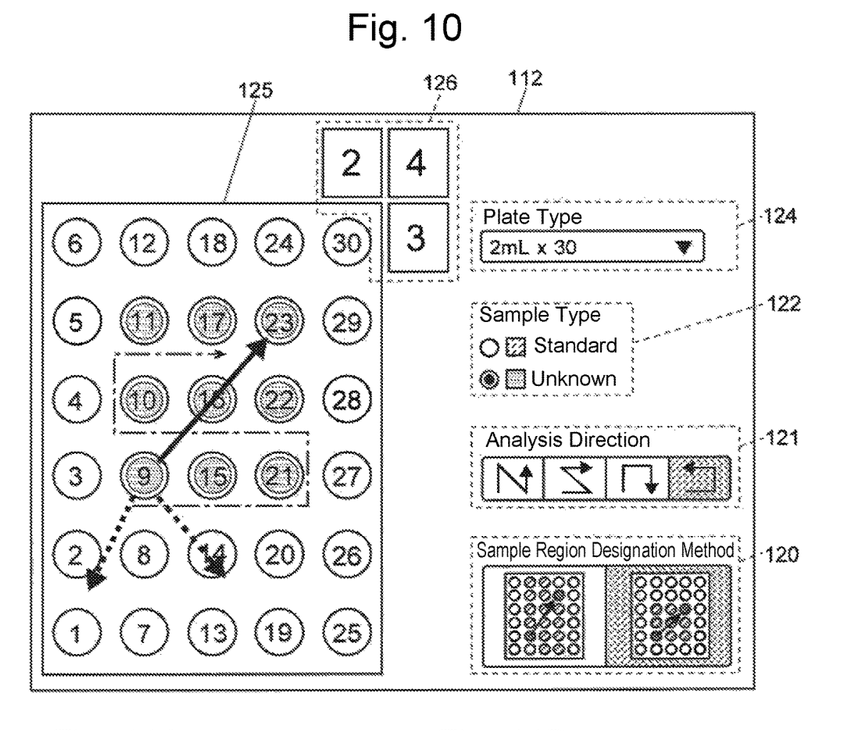
FIG. 10 is a diagram showing an example of mouse movements from the start position in the case of the sample region designation method: a two-dimensional designation type; and the analysis direction: a horizontal two-way direction.

FIG. 8 to FIG. 10 show specific examples. FIG. 8 is a diagram showing an example of valid and invalid mouse movements from the start position in the case where the sample region designation method is the "one-dimensional designation type" and the analysis direction is the "vertical one-way direction". If the vial number [9] is the start position, a movement of the pointing position of the mouse as indicated by a thick solid arrow causes the mouse operation to be valid. Movements of the pointing position of the mouse as indicated by thick broken arrows cause the mouse operations to be invalid. FIG. 9 is a diagram showing an example of valid and invalid mouse movements from the start position in the case where the sample region designation method is the "one-dimensional designation type" and the analysis direction is the "vertical two-way direction". FIG. 10 is a diagram showing an example of valid and invalid mouse movements from the start position in the case where the sample region designation method is the "two-dimensional designation type" and the analysis direction is the "horizontal two-way direction". In all the cases, movements of the pointing position of the mouse as indicated by thick broken arrows cause the mouse operations to be invalid, as with the case of FIG. 8.

Furthermore, during execution of the above step S6, the analysis condition setting screen display processor 322 calculates the region of selected vial-mounting positions based on the pointing position of the mouse obtained in real time, the sample region designation method selected in step S3, and the analysis direction selected in step S4. If the mouse operation is valid, the display colors of vials included in the region in the plate image are changed to a predetermined display color (e.g., red) (step S7). On the other hand, if the mouse operation is determined to be invalid, the display color indicating the selected state is not changed. Accordingly, when the analysis operator appropriately moves the pointing position of the mouse, the region of vials shown in a predetermined display color is changed in real time according to the pointing position. This change allows the analysis operator to intuitively grasp which vials are to be analysis targets. If the display colors of vials are not changed, inappropriateness of the mouse operation can be immediately grasped.

For instance, in the example of FIG. 8, the vials having the vial numbers [9], [10], [11], [12], [13], [14], [15] and [16] are displayed to be in the selected state. Furthermore, in the example of FIG. 9, the vials having the vial numbers [9], [10], [11], [12], [17] and [18] are displayed to be in the selected state. Moreover, in the example of FIG. 10, the vials having the vial numbers [9], [10], [11], [15], [16], [17], [21], [22] and [23] are displayed to be in the selected state. In FIG. 8 to FIG. 10, the order of performing analyses of the selected vials is indicated by an alternate long and short dash line.

As described above, after pointing the start position, the analysis operator moves the pointing position of the mouse, and releases the pressed mouse button in a state where the pointing position of the mouse is on the vial intended to be the end position. Upon receipt of this operation, the analysis condition input processor 321 recognizes, as the end position, the vial number where the operation of releasing the pressed state is performed (step S8). That is, in brief, a drag-and-drop operation by the mouse on the plate image can determine the start position and the end position. If the mouse operation is invalidated, release of the pressed mouse button causes the end position to be recognized as the same position as the start position irrespective of the position of the mouse cursor. When the graphical operations as described above determine the start position and the end position, the vial-mounting positions to be analyzed are also determined. The determined start position and end position are displayed with numerals in fields of the start and end of the vial numbers in the text information input area 111.

Figure 4:
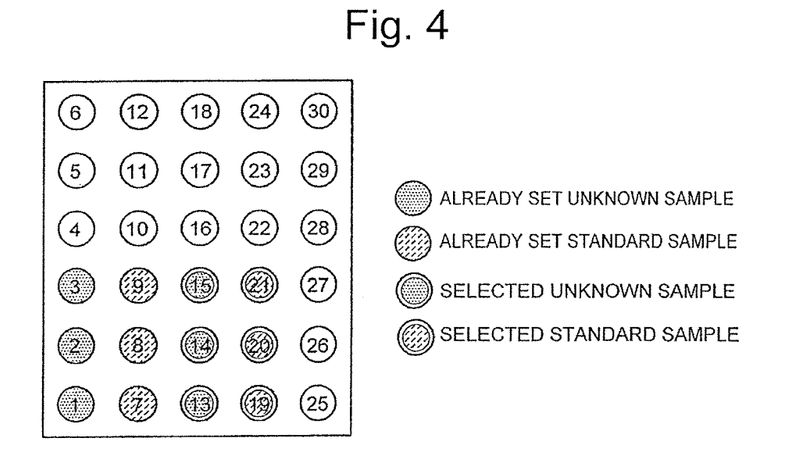
FIG. 4 is a diagram showing an example of a display format of sample types and vial setting states in the LC analyzing system of this example.

When the start position and the end position are determined, the display format of each of the selected vials in the plate image displayed in the plate image display area 125 is changed from the selected state to an already set state. Here, as shown in FIG. 4, in the "selected" state, the display color is provided only at the center of the circular region showing one vial. In the "already set" state, the display color is provided over the entire circular region showing one vial. Accordingly, the analysis operator can easily discriminate the selected vial and the already set vial from each other.

Figure 12:
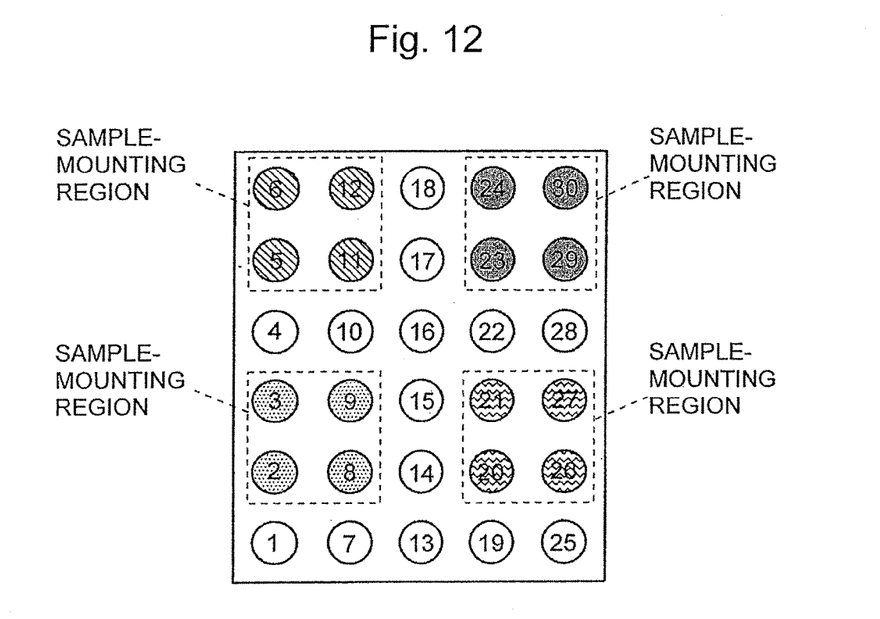
FIG. 12 is a diagram showing an example when analysis target regions are discretely set on the sample plate.

Repetitive execution of the operations of steps S5, S6 and S8 allows multiple analysis target regions to be simultaneously set. In this case, for example, it may be configured such that the operations of steps S5, S6 and S8 are performed while a Ctrl button on the keyboard is pressed in the operation unit 4. For example, as shown in FIG. 12, such repetitive operations also allow multiple analysis target regions to be set at positions apart from each other on one sample plate.

Subsequently, the calculator 323 for the number of samples calculates the number of vials to be analyzed, that is, the number of samples, based on selected information on the sample region designation method, selected information on the analysis direction, and information on the vial numbers indicating the start position and the end position (step S9). The number of samples obtained by the calculation is displayed with numerals in the field of the number of samples in the text information input area 111.

Meanwhile, the analysis operator selects the types of sample in vials included in the analysis target region determined by the operations and processes of steps S3 to S8, through the sample type selecting button 122 (step S10). This example allows selection between the standard sample and the unknown sample, which are displayed in respective colors different from each other. For example, the unknown sample is drawn in red, the standard sample is drawn in green. The aforementioned FIG. 4 shows discrimination between the selected state and the already set state on the display, and also shows discrimination between the unknown sample and the standard sample. Thus, in the plate image displayed on the plate image display area 125, the difference between sample types is also clear.

In the fields of the number of injections and the amount of injection in the text information input area 111, numerals are displayed as default. If the analysis operator intends to change the numerals, this operator may perform a tap operation on an arrow in a spin box or directly input numeral values. The analysis operator sets a method file to be used for analyses in the text information input area 111, and furthermore inputs a sample name, a sample ID and the like as necessary.

After the operations and processes as described above finish the settings of conditions of a series of serial analyses, the analysis operator clicks the batch table creation instructing button 140 to make an instruction for addition of content to the batch table (step S11). Upon receipt of this instruction, the batch table creating processor 324 adds a row to the batch table where one analysis for one vial (sample) is summarized in one row, based on the analysis conditions set in the batch setting area 110 (step S12). At this time, in the vial number fields in the batch table, the numbers of vials to be analyzed are automatically set.

After the batch table is thus completed and the analysis operator clicks the batch analysis start instructing button 150, the batch table having been created or corrected is stored in the batch table storage 325. The analysis controller 31 then controls the liquid chromatograph unit 1 and the auto-sampler 2 according to the stored batch table to start serial analyses.

In the above operations, the operation of selecting the sample region designation method in step S3 is required to be performed before the operations of steps S4 and S5 to S8. If the selection of the sample region designation method is changed after the operations of steps S4 and S5 to S8, the operations of steps S4 and S5 to S8 are required to be performed again. Meanwhile, the order of the operation of step S4 and the operations of steps S5 to S8 may be inverted. If the operation of step S4 is performed again after the operations of steps S5 to S8 are completed and the number of samples is calculated, the end position is recalculated based on the information on selection of the analysis direction, the already set start position, and the number of samples after this change. Accordingly, the analysis operator can simply performs operations without consideration of the order of the operation of step S4 and the operations of steps S5 to S8.

Figure 11A:
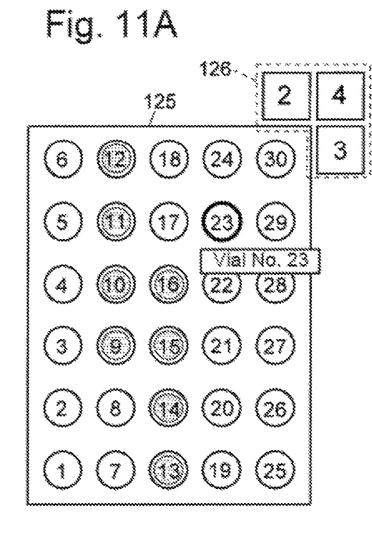
FIG. 11A and FIG. 11B are diagrams showing examples of plate image displays when a sample plate is selected in the case where a plurality of sample plates are used.
Figure 11B:
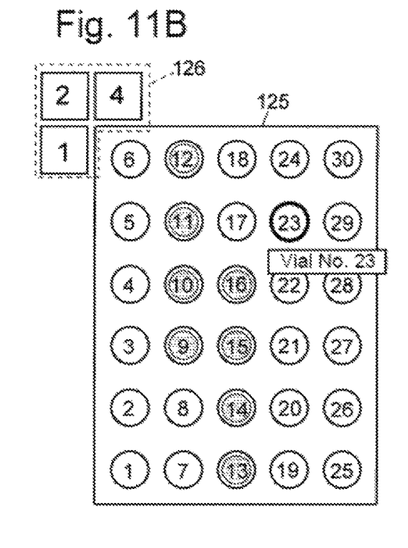

If analysis conditions are intended to be set for vials mounted on different sample plates, it is only required to click a desired number among the sample plate number selecting buttons 126. At this time, the number on the sample plate number selecting button 126 corresponds to the position of the sample plate actually arranged in the auto-sampler 2. Upon designation of a certain number among the sample plate number selecting buttons 126, the plate image is displayed on the sample plate number selecting button 126 at the position for the number (see FIG. 11A and FIG. 11B). Accordingly, the analysis operator can intuitively grasp the correspondence between the numbers of the sample plates and the sample plate on which the operation is actually performed.

The flowchart may be changed such that the selection of the sample plate through the sample plate number selecting button 126 and the selection of the sample type through the sample type selecting button 122 are performed at an appropriate time point before step S11.

It should be noted that the above examples are a mere example of the present invention, and any modification, correction or addition appropriately made within an extent of the spirit of the present invention will evidently fall within the scope of claims of the present patent application. For example, the examples are the LC analyzing system. However, it is a matter of course that the analysis method is not limited to that in the LC, as long as an apparatus or a system that includes an analogous auto-sampler is adopted.

REFERENCE SIGNS LIST

1 . . . Liquid Chromatograph Unit
11 . . . Mobile Phase Container
12 . . . Liquid Transport Pump
13 . . . Injector
14 . . . Column
15 . . . Detector
2 . . . Auto-Sampler
21 . . . Sample Plate
22 . . . Vial
23 . . . Plate Driver
24 . . . Sample Collector
3 . . . Controller
31 . . . Analysis Controller
32 . . . Automatic Analysis Condition Setting Processor
321 . . . Analysis Condition Input Processor
322 . . . Analysis Condition Setting Screen Display Processor
323 . . . Calculator for the Number of Samples
324 . . . Batch Table Creating Processor
325 . . . Batch Table Storage
4 . . . Operation Unit
5 . . . Display Unit
100 . . . Batch Table Setting Screen
110 . . . Batch Setting Area
111 . . . Text Information Input Area
112 . . . Graphical Information Input Area
120 . . . Sample Region Designation Method Selecting Button
121 . . . Analysis Direction Selecting Button
122 . . . Sample Type Selecting Button
124 . . . Plate Type Setting Field
125 . . . Plate Image Display Area
126 . . . Sample Plate Number Selecting Button
130 . . . Batch Table Display Area
140 . . . Batch Table Creation Instructing Button
150 . . . Batch Analysis Start Instructing Button

The invention claimed is:

1. An automatic analyzer comprising:
an auto-sampler that sequentially selects samples one after another previously prepared on a sample plate on which the samples are mountable two-dimensionally in rows and columns and take at least a part of the samples,
an analyzer that analyzes the taken samples, and
a control apparatus including;
a) a display processor configured to display a plate image indicating a shape of the sample plate used for analysis and sample-mountable positions on the sample plate, on a screen of a display unit;
b) a first selector configured to allow an analysis operator to select a type as an analysis target region designation method to designate either a linear or a rectangular region as an analysis target region where the samples to be subjected to serial analyses are mounted on the sample plate;
c) a second selector configured to allow the analysis operator to select an analysis direction on the sample plate during the serial analyses from among a plurality of options;
d) a start/end position recognizer configured to recognize a start position of a sample on the sample plate where the serial analyses are started according to a first operation performed by the analysis operator using a pointing device on the plate image displayed on the screen of the display unit, and to recognize an end position of a sample on the sample plate where the serial analyses are finished according to a second operation performed by the analysis operator using the pointing device on the plate image;
e) a sample-number calculator configured to calculate the number of samples to be serially analyzed based on the analysis target region designation method selected by the first selector, the analysis direction selected by the second selector, and the start position and the end position recognized by the start/end position recognizer; and
f) a batch table creator configured to create a batch table including descriptions about control information for performing the serial analyses and to identify respective identification numbers of mounting positions on the sample plate of the samples to be analyzed in the serial analyses, based on the analysis target region designation method selected by the first selector, the analysis direction selected by the second selector, the start position and the end position recognized by the start/end position recognizer, and the number of samples calculated by the sample-number-calculator, and sets the identification numbers on respective rows of the batch table,
wherein the control apparatus sequentially takes the samples based on the batch table and wherein the display processor displays samples on the plate image differently between samples already set in the batch table, samples not yet set in the batch table, and samples being selected for designating the start position and the end position.

2. The automatic analyzer according to claim 1,
wherein the display processor repeatedly calculates the region of selected samples based on a latest pointing position by the pointing device while the pointing device is being moved after the first operation for designating the start position and the end position is performed using the pointing device on the plate image, and displays the plate image such that samples determined to be selected by the calculation is visually discriminable from other samples.

3. The automatic analyzer according to claim 1,
wherein the apparatus further includes a third selector for allowing the analysis operator to select one from options of sample information on the samples, where the options include at least a standard sample and an unknown sample, and
the display processor displays the plate image such that at least the standard sample and the unknown sample are visually discriminated from each other based on the sample information already set using the third selector or the sample information to be set using the third selector.

4. The automatic analyzer according to claim 1,
wherein the start/end position recognizer invalidates the second operation by the analysis operator using the pointing device when the pointing position by the pointing device is at a position out of a region that can be allowed according to the analysis direction selected by the second selector while the pointing device is being moved after the first operation is performed using the pointing device on the plate image.

5. The automatic analyzer according to claim 1,
wherein the order of an operation for the selection of the analysis direction by the second selector and an operation for the designation of the start position and the end position by the start/end position recognizer can be exchanged.

6. The automatic analyzer according to claim 1,
wherein discontinuous sample-mounted positions can be set according to a predetermined operation.

7. The automatic analyzer according to claim 1,
wherein the auto-sampler can be loaded with a plurality of sample plates,
the apparatus further comprises:
   a fourth selector for allowing the analysis operator to select a type of the sample plate to be used for serial analyses; and
   a fifth selector for allowing the analysis operator to select one sample plate with reference to sample plate numbers assigned to the respective sample plates when the sample plates are loaded in the auto-sampler, and
the display processor displays, on the screen of the display unit, the plate image according to the type selected by the fourth selector, when the one sample plate classified into the type is selected by the fifth selector.

8. The automatic analyzer according to claim 7,
wherein the display processor displays, on the screen of the display unit, correspondence relationship between positions of the sample plates in the auto-sampler and the respective sample plate numbers.

9. The automatic analyzer according to claim 1,
wherein the auto-sampler can be loaded with a plurality of sample plates, and
the apparatus further comprises an information acquisition unit that receives information on types and loading positions of one or more sample plates from the auto-sampler when the one or more sample plates are loaded in the auto-sampler, and the display processor displays the plate image corresponding to the designated sample plate number based on the information received by the information acquisition unit.

* * * * *